United States Patent [19]

Albright

[11] 4,163,005
[45] Jul. 31, 1979

[54] HALOBENZENE SULFONATE FLAME RETARDANTS

[75] Inventor: James A. Albright, Ann Arbor, Mich.

[73] Assignee: Velsicol Chemical Corporation, Chicago, Ill.

[21] Appl. No.: 823,773

[22] Filed: Aug. 11, 1977

[51] Int. Cl.$^2$ .................. C07C 143/68; C08K 5/42
[52] U.S. Cl. .................. 260/45.7 S; 260/45.75 B; 260/456 P; 521/121; 521/906; 528/48
[58] Field of Search .................. 260/45.7 SF, 456 P; 521/121 (U.S. only)

[56] References Cited

U.S. PATENT DOCUMENTS

| | | | |
|---|---|---|---|
| 2,028,715 | 1/1936 | Hanson | 260/45.7 RL |
| 2,485,095 | 10/1949 | Harris et al. | 260/456 P |
| 2,486,416 | 11/1949 | Jackson | 260/456 P |
| 2,678,878 | 5/1954 | Stewart | 71/77 |
| 3,551,360 | 12/1970 | Dressler | 260/45.7 S |
| 3,850,972 | 11/1974 | Goralski | 106/15 FP |
| 3,945,954 | 3/1976 | Batorewicz | 260/2.5 AJ |
| 4,038,245 | 7/1977 | Reineke | 260/45.7 SF |
| 4,046,719 | 9/1977 | Stanaback et al. | 260/45.7 P |
| 4,052,346 | 10/1977 | Rudner et al. | 521/121 |

OTHER PUBLICATIONS

Hilado, Flammability Handbook for Plastics, 1969, pp. 84 and 85.

Primary Examiner—Hosea E. Taylor
Assistant Examiner—R. A. White
Attorney, Agent, or Firm—Dietmar H. Olesch; Howard J. Greenwald

[57] ABSTRACT

Disclosed are halobenzene sulfonates, and flame resistant polymer compositions containing the sulfonates.

13 Claims, No Drawings

HALOBENZENE SULFONATE FLAME RETARDANTS

BACKGROUND OF THE INVENTION

1. Field of the Invention

This invention relates to certain halobenzene sulfonates and to flame retardant polymeric compositions containing these compounds.

2. Description of the Prior Art

During the past several years, a large number of flame retardants have been developed for use with an almost equally large number of flammable materials. Cellulosic materials such as paper and wood and polymeric materials such as synthetic fibers and bulkier plastic articles are just two examples of materials for which flame retardants have been developed. For any class of flammable materials, such as synthetic high polymers, those skilled in the art have long been aware that some flame retardant additives are more effective in some polymers than they are in others. In fact, many flame retardant additives which are highly effective in some polymer systems are virtually ineffective in other polymer systems. The mere fact, therefore, that certain compounds contain halogen and sulfur atoms does not assure that any given halogenated or sulfur containing compound will impart useful flame retardant characteristics to all or even to any polymeric systems. Furthermore, as those skilled in the art have improved the flame retardancy of polymeric materials, they have been simultaneously required to provide the necessary flame retardancy with a minimal effect upon other properties of the polymers such as their light stability, moldability and flexural, tensile and impact strengths. Balancing all of the foregoing considerations and thereby developing polymeric compositions with good flame retardant characteristics as well as a satisfactory balance of other properties is, consequently, a task which has in the past and presently continues to require the exercise of a high degree of inventive skill.

The prior art considered in connection with the preparation of this application in U.S. Pat. No. 2,412,116 to Baker, Jr., U.S. Pat. No. 2,412,117 to Baker, Jr., U.S. Pat. No. 2,485,095 to Harris et al., U.S. Pat. No. 2,486,417 to Jackson et al., U.S. Pat. No. 2,567,008 to Britton et al., U.S. Pat. No. 2,683,161 to Knowles et al., U.S. Pat. No. 2,894,971 to O'Rear et al., U.S. Pat. No. 3,021,944 to Buecheler et al., U.S. Pat. No. 2,962,514 to Carbon et al., U.S. Pat. No. 3,395,232 to White, U.S. Pat. No. 3,850,972 to Goralski, and U.S. Pat. No. 3,914,272 to Starks et al.

In particular U.S. Pat. No. 2,412,116 teaches phenyl sulfonyl diesters of nitro alcohols having the general formula

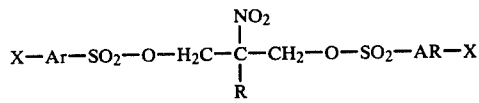

wherein R is hydrogen or alkyl, Ar is a phenyl nucleus, and X is hydrogen, alkyl, and acylamino. These compounds are taught as plasticizers for synthetic rubber and similar type polymers.

U.S. Pat. No. 2,412,117 teaches phenyl sulfonyl triesters of nitro alcohols having the general formula

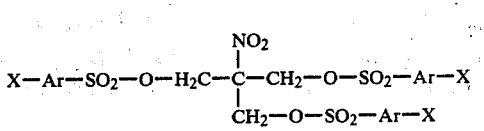

wherein Ar is phenyl nucleus and X is hydrogen, alkyl and acylamino. These compounds are taught as being plasticizers for synthetic rubber and similar type polymers.

U.S. Pat. No. 2,485,095 teaches beta-monohaloethyl esters of manohalogenated benzene sulfonic acids having the formula

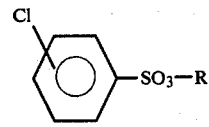

wherein R is monohaloethyl. These compounds are disclosed as being useful as insecticides.

U.S. Pat. No. 2,486,417 teaches alkylbenzene sulfonic acid esters having the formula

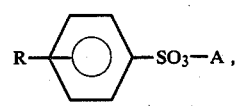

wherein R is an alkyl group containing 1 to 8 carbon atoms and A is an alkyl or aryl group derived from mono-and polyhydroxy acyclic and cyclic hydrocarbon compounds such as the normal acohols, the alkylene glycols, and the phenols and homologues thereof. These compounds are taught as being useful as plasticizers.

U.S. Pat. No. 2,894,971 teaches polyfluoroalkyl -p-toluenlsulfonates having the general formula

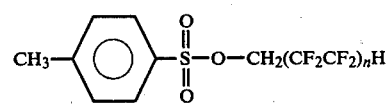

wherein n is an integer from 3 to 10. These compounds are disclosed as being useful heat transfer fluids.

U.S. Pat. No. 3,914,272 discloses lower alkyl arylsulfonates having the formula

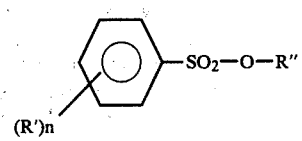

wherein n is zero or one, R' is a halogen or a $C_1$ to $C_4$ alkyl group, and R'' is a $C_1$ to $C_4$ alkyl group. These compounds are taught as being useful in a process for exchanging alkyl moieties between compounds comprising reacting lower alkyl arylsulfonates with a higher alkyl halide in the presence of an organic quaternary salt.

The compounds of the instant invention are better flame retardants and/or have greater thermal and/or hydrolytic stability than these prior art compounds.

SUMMARY OF THE INVENTION

In accordance with this invention there are provided hydrolytically and/or thermally stable halobenzene sulfonates of the formula

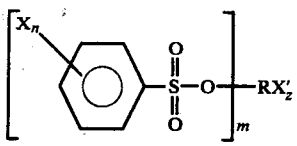

wherein X and X' are independently selected halogens, preferably chlorine and bromine; n is an integer of from 1 to 5; R is an alkyl or alkenyl of from 3 to about 8 carbon atoms; z has a value of 0 if Y−Y'=0 and a value of from 1 to L if Y− Y'>0, wherein L=Y−Y''+W, with Y being the number of primary, secondary, and tertiary carbon atoms in R, Y' being the number of primary, secondary and tertiary carbon atoms in R containing a halobenzene sulfonate substituent, and W=A−B wherein A is the number of replacable hydrogen atoms present on the primary, secondary and tertiary carbon atoms in R devoid of halobenzene sulfonate substituents and B is the number of primary, secondary and tertiary carbon atoms in R devoid of halobenzene sulfonate substituents; and m is an integer of from 2-4, provided that m is an integer of from 1-4 when R is a neopentyl group. Also provided is a flame retardant plastic composition comprised of a polymer and said halobenzene sulfonates.

DESCRIPTION OF THE PREFERRED EMBODIMENTS

In accordance with this invention there are provided halobenzene sulfonates of the formula

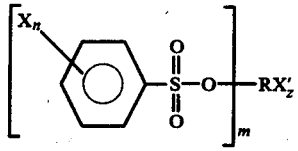

wherein X and X' are independently selected halogen, preferably chlorine and bromine; n is an integer of from 1 to 5; R is an alkyl or alkenyl of from 3 to about 8 carbon atoms; z has a value of 0 if Y−Y'=0 and when Y−Y'>0 z is an integer of from 1 to L, wherein L=Y−Y'+W, wherein Y is the number of primary, secondary, and tertiary carbon atoms in R, Y' is the number of primary, secondary, and tertiary carbon atoms in R containing a halobenzene sulfonate substituent, and W=A−B wherein A is the number of replacable hydrogen atoms present on the primary, secondary and tertiary carbon atoms in R devoid of halobenzene sulfonate substituents and B is the number of primary, secondary and tertiary carbon atoms in R devoid of halo- benzene sulfonate substituents; and m is an integer of from 2-4, provided that m is an integer of from 1-4 when R is a neopentyl group. For purposes of the present invention a primary carbon atoms is a carbon atom which is attached to only one other carbon atom, a secondary carbon atom is a carbon atom which is attached to two other carbon atoms, and a tertiary carbon atom is a carbon atom which is attached to three other carbon atoms. Compounds of formula I wherein Z has a value of from 1 to L are preferred.

A more preferred class of compounds falling within formula I are those having the subgeneric formula

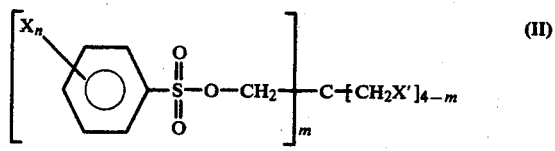

wherein X, X' and n are as defined above and wherein m is an integer of from 1 to 4. Compounds of formula II wherein m is 2 to 3 are most preferred. These compounds of formula II have excellent thermal and hydrolytic stability.

Exemplary compounds falling within the scope of formula I include 1,4-bis-(2',4',6'-trichlorobenzene sulfonato)-2,3-dibromo-2-butene, 1,4-bis-(2',5'-dibromobenzene sulfonato)-2,3-dibromo-2-butene, 1,4-bis-(2',4',6'-trichlorobenzene sulfonato)-2,3-dibromobutane, 1,4-bis-(2',5'-dibromobenzene sulfonato)-2,3-dibromobutane, 1,3-bis-(2',4',6'-tribromobenzene sulfonato)-2-bromopropane, 1,3,5-tris-2',5'-dibromo-benzene sulfonato)-2,4-dichloropentane, 1,3,5-tris-(2',4',6'-trichlorobenzene sulfonato)-2,4-dibromo-2-pentene, 1,4-bis-(2',4',6'-trichlorobenzene sulfonato)-2,2,3,3-tetrabromobutane and 1,3-bis-(2',5'-dibromobenzene sulfonato)-3-bromomethyl propane. Exemplary preferred compounds falling within formula II include tris-(2,2,2-bromomethyl) ethyl-2',4',5'-trichlorobenzene sulfonate, tris-(2,2,2-bromomethyl) ethyl-2',5'-dibromobenzene sulfonate, 1,3-bis-(2',4',5'-trichlorobenzene sulfonato)-2,2-bis-(bromomethyl) propane, and 1,3-bis(2',5'-dibromobenzene sulfonato)-2,2-bis-(bromomethyl) propane.

For purposes of illustration only, Table I is designed to further help describe the compounds of this invention and is neither meant nor should it be taken to be a complete listing of all the compounds within the scope of this invention as described by formulas I and II. In Table I below the unsatisfied valences on the carbon atoms under the heading RX$_z$ are representative of the points of attachment of the halobenzene sulfonate groups.

The halobenzene sulfonate compounds within the scope of this invention may be prepared according to the following reaction schemes:

Equation A

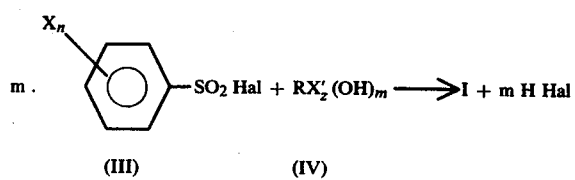

-continued

Equation B

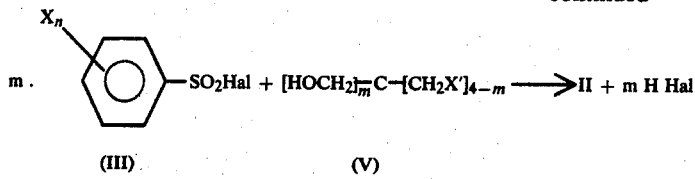

$m \cdot$ (III) $-SO_2Hal + [HOCH_2]_{\overline{m}}C-[CH_2X']_{4-m}$ (V) $\longrightarrow$ II + m H Hal wherein X, X', n, m and z are as defined above and Hal is a halogen, preferably chlorine or bromine.

More particularly, the reaction of Equation A is generally carried out by the reaction of m moles of compound of formula III with one mole of compound of formula IV. The reaction conditions are such as to facilitate the coreaction of compound III with compound IV to produce compound I. Generally, the reaction can be carried out at a temperature between 0° to about 150° C. and preferably from about 60° to about 120° C. The reaction can be carried out using an organic tertiary amine base as a catalyst and hydrogen halide acceptor, e.g., triethylamine, pyridine. The reaction can be carried out in an inert organic solvent, e.g., toluene, dimethylformamide, dimethylsulfoxide, benzene, etc. Atomospheric or superatomspheric pressures are generally preferred. The reaction is generally carried out from 1 to 48 hours but the time is generally dependent on the other reaction conditions such as temperature, pressure, etc.

Also more particularly, the reaction of Equation B is generally carried out by the reaction of m moles of compound III with one mole of compound V. As with the reaction of Equation A, the reaction conditions existant during the reaction of Equation B are such as to facilitate the coreaction of compound III with compound V to produce compound II. Generally, this reaction can be carried out at a temperature between 0° to about 150° C. and preferably from about 60° to about 120° C. The reaction can be carried out using an organic tertiary amine base as a catalyst and hydrogen halide acceptor, e.g., triethylamine, pyridine, etc. The reaction can be carried out in an inert organic solvent, e.g., toluene, dimethylformamide, carbon tetrachloride, dimethylsulfoxide, benzene, etc. Atmospheric or superatmospheric pressures are generally preferred. The reaction is generally carried out from 1 to 48 hours but the time is generally dependent on the other reaction conditions such as temperature, pressure, etc.

TABLE I

| Compound | $\left[\begin{array}{c} X_n \\ \bigcirc \\ \end{array} \begin{array}{c} O \\ \parallel \\ S-O- \\ \parallel \\ O \end{array}\right]_m$ | n | m | z | $RX'_z$ |
|---|---|---|---|---|---|
| 1 | 2',3',4',5',6'-pentachlorobenzene sulfonate | 5 | 2 | 2 | $-CH_2-CBr_2-CH_2-$ |
| 2 | 2',6'-dichloro-4'-bromobenzene sulfonate | 3 | 3 | 0 | $-CH_2-\overset{\|}{CH}-CH_2-$ |
| 3 | 2',4'-dibromobenzenesulfonate | 2 | 3 | 3 | $-CH_2-CHBr-\overset{\|}{CH}-CHBr-CH_2-$ |
| 4 | 3'-bromobenzene sulfonate | 1 | 4 | 4 | $\rangle CH-CH_2Br-CBr_2-CHBr-CH\langle$ |
| 5 | 2',3',4',5',6'-pentabromobenzene sulfonate | 5 | 4 | 2 | $CH_2Br-\overset{\|}{CH}-\overset{\|}{CH}-\overset{\|}{CH}-\overset{\|}{CH}-CH_2Br$ |
| 6 | 2',5'-dibromobenzene sulfonate | 2 | 3 | 1 | $-H_2C-\overset{Br}{\underset{\|}{C}}-CH_2-$ with $-CH_2$ and $-CH_2$ substituents |
| 7 | 2'-chloro-4',6'-dibromobenzene sulfonate | 3 | 4 | 0 | $-H_2C-\overset{-CH_2}{\underset{-CH_2}{C}}-CH_2-$ |
| 8 | 2',3'-dibromo-5',6'-dichlorobenzene sulfonate | 4 | 2 | 2 | $CH_3-CH_2Br-\overset{\|}{C}-CH_2Br-CH_3$ |
| 9 | 2',4',6'-tribromobenzene sulfonate | 3 | 1 | 1 | $-CH_2-\overset{CH_3}{\underset{CH_3}{\overset{\|}{C}}}-CH_2Br$ |
| 10 | 2',5'-dibromobenzene sulfonate | 2 | 1 | 3 | $-CH_2-\overset{CH_2Br}{\underset{CH_2Br}{\overset{\|}{C}}}-CH_2Br$ |

TABLE I-continued $$\left[ \begin{array}{c} X_n \\ \phantom{X}\bigcirc\!\!\!\!\!\!-\!\!\!\overset{\overset{O}{\|}}{\underset{\underset{O}{\|}}{S}}\!-\!O- \end{array} \right]_m RX'_z$$

| Compound | | n | m | z | RX'$_z$ |
|---|---|---|---|---|---|
| 11 | 2′,5′-dibromobenzene sulfonate | 2 | 2 | 2 | $-CH_2-\underset{\underset{CH_2Br}{\|}}{\overset{\overset{CH_2Br}{\|}}{C}}-CH_2-$ |
| 12 | 2,4′,6′-tribromobenzene sulfonate | 3 | 2 | 1 | $-CH_2-CHCl-CH_2-$ |
| 13 | 2′,4′,5′-trichlorobenzene sulfonate | 3 | 2 | 2 | $-CH_2-\underset{\underset{CH_2Br}{\|}}{\overset{\overset{CH_2Br}{\|}}{C}}-CH_2-$ |
| 14 | 2′,4′,5′-trichlorobenzene sulfonate | 3 | 1 | 3 | $-CH_2-\underset{\underset{CH_2Br}{\|}}{\overset{\overset{CH_2Br}{\|}}{C}}-CH_2Br$ |
| 15 | 2′,4′,5′-trichlorobenzene sulfonate | 3 | 2 | 2 | $-CH_2CHBrCHBrCH_2$ |
| 16 | 2′,5′-dibromobenzene sulfonate | 2 | 2 | 2 | $-CH_2-\overset{\overset{Br}{\|}}{C}=\overset{\overset{Br}{\|}}{C}-CH_2$ |

The compounds of formula I and subgeneric formula II are useful flame retardants in polyolefin polymers, such as polypropylene, polyurethane, including flexible and rigid foams and elastomers, and styrene polymers such as polystyrene, including both crystalline and high impact types, and styrene co- and terpolymers such as styrene-butadene copolymer, styrene-acrylonitrite copolymer and acrylonitrite-butadiene-styrene terpolymers. A further description of the above polymers applicable to the present invention may be found in Modern Plastics Encyclopedia, Vol. 52, No. 10A, McGraw-Hill, Inc., New York, N.Y. (1975), said publication being incorporated herein by reference.

It is also contemplated that the flame retardants of this invention will possess excellent flame retardant efficacy in polyesters, both saturated and unsaturated polyesters. A detailed description of polyester polymers can be found in Modern Plastics Encyclopedia, Ibid., Said Encyclopedia having been incorporated herein by reference.

Generally the flame retardants of this invention may be incorporated into or applied onto virtually any flammable polyurethane, polyolefin, and styrene polymeric material by techniques which are standard or known to those skilled in the art. See, for example, J. M. Lyons, "The Chemistry and Uses of Fire Retardants", Wiley-Interscience, New York, N.Y. (1970), and Z. E. Jolles, "Bromine and It's Compounds", Academic Press, New York, N.Y. (1966). The amount of the flame retardant compound of the present invention incorporated into the polymeric system is an amount effective to render said polymeric system flame retardant. Generally, this is, in percent by weight, from about 1% to about 50%. Usually, depending on the substrate and the amount of flame retardancy desired, up to about 40 weight percent of the flame retardant compound within the scope of this invention can be incorporated therewith. However, in most applications it is preferred to use less than 25 weight percent of said compounds within the scope of this invention. It should be noted that the optimum level of additive of the flame retardant within the scope of this invention depends upon the particular substrate being treated as well as the level of flame retardancy desired. For example, in polyurethanes a flame retardant level of from about 10 to 35 percent by weight of the total polymeric composition is satisfactory.

In addition to the flame retardant compounds within the scope of this invention, the flame retardancy of a polymer can be further enhanced through the use of so-called "synergists" or enhancing agents which when used with the compounds of formula I or II promote a cooperative effect therebetween and thus enhance the flame retardancy of the resultant plastic composition as compared to the flame retardancy of either one component used separately. These "enhancing agents" comprise the oxides and halides of groups IVA and VA of the Periodic Table, I.e., oxides and halides of antimony, bismuth, arsenic, tin, lead, germanium, e.g., antimony oxychloride, antimony chloride, antimony oxide, stannic oxide, stannic chloride, arsenous oxide, arsenous chloride, and the like; and organic and inorganic compounds of phosphorus, nitrogen, boron, and sulfur, e.g., triphenyl phosphate, ammonium phosphate, zinc borate, thiourea, urea, stannic sulfide, and the like and oxides and halides of titanium, vanadium, chromium, manganese, iron, niobium, molybdenum copper, zinc, magnesium, e.g., titanium dioxide, titanium chloride, vanadium pentoxide, chromic bromide, manganous oxide, molybdenum trioxide, ammonium molybdate; and hydrates of the above, e.g., stannic oxide hydrate, lead hydrate; and combinations thereof. The preferred enhancing agents are the oxides of antimony, arsenic and bismuth. However, any compound which on decomposition, as by ignition, yields these oxides would be suitable. Thus, some organic antimonates are preferred. The enhancing agents disclosed in U.S. Pat. No. 3,205,196 are also suitable for use.

U.S. Pat. No. 3,205,196, column 2, states that "Antimony oxide is the antimony compound that is presently preferred for use in the present invention. However, many antimony compounds are suitable. Inorganic antimony compounds include antimony sulfide, sodium antimonite, potassium antimonite, and the like. Many organic antimony compounds are suitable such as the antimony salts of organic acids and their pentavalent derivatives disclosed in . . . Pat. No. 2,996,528. Compounds of this class include antimony butyrate, antimony valerate, antimony heptylate, antimony hepthlate, antimony caprylate, antimony pelargonate, antimony caprate, antimony cinnamate, antimony anisate, and their pentavalent dihalide derivatives. Likewise, the esters of antimonous acids and their pentavalent derivatives disclosed in ... Pat. No. 2,993,924, such as tris(n-octyl) antimonite, tris(2-ethylhexyl) antimonite, tribenzyl antimonite, tris(β-chloroethyl) antimonite, tris (βchlorobutyl) antimonite and their pentavalent compounds and the cyclic antimonites such as trimethylolpropane antimonite, pentaerythritol antimonite, and glycerol antimonite. The corresponding arsenic and bismuth compounds can also be employed."

It is to be understood that such patents as U.S. Pat. Nos. 3,205,196; 2,996,528 and 2,993,924 are to be considered as incorporated herein by reference for all intents and purposes. Without limitation, preferred enhancing agents include $Sb_2O_3$, $SbCl_3$, $SbBr_3$, $SbI_3$, $SbOCl$, $As_2O_5$, $ZnBO_4$, $BaB_2O_4 \cdot H_2O$, $2 \cdot ZnO \cdot 3B_2O_3 \cdot 3.5H_2O$ and stannic oxide hydrate. The more preferred enhancing agent is antimony trioxide.

It is also within the scope of the present invention to employ other materials in the present invention compositions (wood one so desires to achieve a particular end result. Such materials include, without limitation, adhesion promotes; anti-oxidants; antistatic agents; antimicrobials; colorants; flame retardants such as those listed on pages 665–668; Modern Plastics Encyclopedia, ibid., (in addition to the new class of flame retardants described herein); heat stabilizers; light stabilizers; pigments; plasticizers; preservatives; (asbestos, stabilizers and fillers.

In this latter category, i.e., fillers, there can be mentioned without limitation, materials such as glass, carbon; cellulosic fillers (wood flour, cork and shell flour); calcium carbonate (chalk, limestone, and precipitated calcium carbonate); metal flakes; metallic oxides (aluminum, beryllium oxide and magnesia); metallic powders (aluminum, bronze, lead, stainless steel and zinc); polymers (comminuted polymers and elastomerplastic blends); silica products (diatomaceous earth, novaculite, quartz, sand, tripoli, fumed colloidal silica, silica aerogel, wet process silica); silicates (asbestos, kaolinite, mica, nepheline, syenite, talc, wollastonite, aluminum silicate and calcium silicate); and inorganic compounds such as barium ferrite, barium sulfate, molybdenum disulfide and silicon carbide. The above mentioned materials, including filler, are more fully described in Modern Plastics Encyclopedia, ibid., which publication has been incorporated herein by reference.

The amount of the above described materials employed in the present invention compositions can be any quantity which will not substantially adversely affect the desired results derived from the present invention compositions. Thus, the amount used can be any amount up to that percent based on the total weight of the composition at which said composition can still be classified as a plastic. In general, such amount will be from about 0% to about 75% and more specifically from about 1% to about 50%.

The following examples are provided for the purpose of further illustration only and are not intended to be limitations on the disclosed invention. Unless otherwise specified, all temperatures are expressed in degrees centigrade; all weights are expressed in grams; and all volumes are expressed in milliliters.

EXAMPLE 1

Preparation of tris-(2,2,2-bromomethyl) ethyl-2',4',5'-trichlorobenzene sulfonate.

To a solution of 15 grams of 2,4,5-trichlorobenzene sulfonyl chloride dissolved in 20 ml of pyridine was added 16 grams of tribromoneopentyl alcohol. The solution was stirred and heated at 65° C. for 4 hours. The solution was then cooled to 0° C. and diluted with 200 ml of water. A tan solid separated and was washed three times with water. After drying, 22 grams of a tan solid resulted having a melting point of 115°–118° C.

NMR analysis confirmed that this was tris-(2,2,2-bromomethyl) ethyl-2',4',5'-trichlorobenzene sulfonate.

In a similar manner tris-(2,2,2-bromomethyl)ethyl-2',5'-dibromobenzene sulfonate is prepared when 2,5-dibromobenzene sulfonyl chloride is used as the starting material.

EXAMPLE 2

Preparation of 1,3-bis-(2',4',5'-trichlorobenzene sulfonato)-2,2-bis-(bromomethyl)propane.

Dibromoneopentyl glycol (52 grams) was added to a solution of 120 grams of 2,4,5-trichlorobenzene sulfonyl chloride in 150 ml of pyridine. The resultant solution was heated at 80° C. for 4 hours and cooled to room temperature. Upon diluting this solution with 300 ml of water, a white solid separated and was filtered. After washing with 200 ml of acetone, 40 grams of a white solid was recovered with a melting point of 205°–207° C. This material was found to contain 20.4% bromine and 28.6% chlorine (theory % bromine=21.6 and % chlorine=28.2). NMR analysis confirmed that this material was 1,3-bis-(2',4',5'-trichlorobenzene sulfonato)-2,2-bis-(bromomethyl) propane.

In similar manner 1,3-bis(2',5'-dibromobenzene sulfonato)-2,2-bis(bromomethyl) propane is prepared when the starting material is 2,5 dibromobenzene sulfonyl chloride.

EXAMPLE 3

A rigid polyurethane foam was prepared using the following basic formulation:

| Component | Parts by weight |
|---|---|
| Polyol[a] | 100 |
| Silicone Glycol[b] Surfactant | 2 |
| Trichlorofluoromethane[c] | 35 |
| Polyisocyanate[d] | 135 |

[a]alkanolamine polyol, molecular weight approximately 3500, hydroxyl number approximately 530, Thanol R-350-X Jefferson Chemical Co., Houston, Texas.
[b]Dow Corning 193, Dow Corning Corp., Midland, MI.
[c]Freon 11B, E.I. DuPont de Nemours & Co., Wilmington, Del.
[d]Polymeric Aromatic isocyanate, 31.5% available NCO, Mondur MRS, Mobay Chemical Co., Pittsburgh, PA.

The polyol, surfactant, and flurocarbon blowing agent were combined in a master batch based on 1000 g of polyol to minimize lost of blowing agent.

The following procedure was used to prepare the foam:

1. The polyisocyanate was weighed into a tared, 10 ounce, paper cup (allowances being made for hold-up) and the cup set aside while the remaining ingredients were weighed out and mixed.
2. The polyol masterbatch was weighed out, in the proper amount to give 100 grams of polyol, in a one quart, untreated, paper cup.

3. The 30 grams of the compound of Example I were then weighed into the same one quart cup.
4. The contents of the one quart cup were mixed at 1000 rpm for 5 seconds.
5. The polisocyanate was then added and stirring at 1000 rpm continued for 10 seconds.
6. The mix was poured into a 5 pound, untreated, paper tub and allowed to rise.

After the foam was tack-free, and substantially cured, it was set aside for at least seven days prior to subjecting said foam to an Oxygen Index Test, ASTM D-2863- 70 reported in Table II Table II

| Flame Retardant | Load Level, php | O.I., % |
|---|---|---|
| Control | 0 | 21.0 |
| compound of Example 1 | 30 | 23.0 |

EXAMPLE 4

A solution of 600 grams of polystyrene and 10 parts per hundred resin (phr) of the compound of Example 1 in 2,670 grams of methylene chloride and 60 grams of hexane was prepared. To the above solution was added 3 grams of dicumyl peroxide as a flame retardant synergist. This mixture was poured into an aluminum dish and the methylene chloride was allowed to evaporate in the air. Following this, the casting was steamed to produce a crude foam. This foam was then cut into sufficient specimens of appropriate sizes in order to subject said foam to an Oxygen Index Test (O.I.), ASTM D-2863-70.

Additional samples of polymer were prepared in which the amount of fire retardant was 5 phr and 0 phr (control). The results obtained by subjecting the foamed specimens to the Oxygen Index Test are listed in Table III.

Table III

| Flame Retardant | phr | O.I. |
|---|---|---|
| (control) | 0 | 19.5 |
| Compound of Example 1 | 5 | 24.0 |
| Compound of Example 1 | 10 | 25.5 |

EXAMPLE 5

A polypropylene plastic material, (Hercules 6823 grade of Pro-Fax ® polypropylene) was utilized as the base resin in order to prepare two formulations (plastic compositions). With the exception of formulation No. 1, which was the base resin, 1,3-bis-(2',4',5'-trichlorobenzene sulfonato)-2,2-bis-(bromomethyl) propane (compound 13 in Table I) and antimony trioxide enhancing agent were incorporated into the plastic by dry blending in a Brabender "Prep-Center" fitted with a high shear compounding mixer. The formulations were compounded at 400° F., 120 rpm, with a 2 to 3 minute compounding time.

Each of the two formulations was discharged from the mixer and were injection molded using a Newbury 30 Ton Injection Molding Machine. The following is a set of standard injection molding conditions by which the two formulations were injection molded.
Rear Zone—410° F.
Front Zone—440° F.
Nozzel—140° F.
Injection Speed—4 to 5 seconds
Cycle Time—60 seconds
Mold Temperature—86° F.
Flow Mold Time—1 to 2 seconds These two above prepared formulations were subjected to an Oxygen Index Test, ASTM D-2863-70. The results obtained by subjecting these formulations as well as the percentages by weight based on the total composition of each component utilized in the respective formulations, are listed in Table IV below.

Table IV

| Formulation No. | % 1,3-bis-(2',4',5'-tri-chlorobenzene sulfonato)-2,2-bis-(bromomethyl)propane | % antimony trioxide | O.I. |
|---|---|---|---|
| 1 | 0 | 0 | 18 |
| 2 | 20 | 5 | 21.5 |

EXAMPLE 6

The thermal stability of tris-(2,2,2,-bromomethyl) ethyl-2',4',5'-trichlorobenzene sulfonate, 1,3-bis-(2',4',5'-trichlorobenzene sulfonato)-2,2-bis-(bromoethyl)propane, and beta-chloroethyl-2',4',5'-trichlorobenzenesulfonate was determined by the procedure set forth in section 9-951, "Thermogravimetric Analyzer", of "Instruction Manual 990, Thermal Analyzer and Modules", E. I. DuPont De Nemours and Co. (Inc.), Instrument Products Division, Wilmington, Del. 19898. The results of the thermogravimetric analysis (TGA) of the three compounds at several different weight losses are tabulated in Table IV below. Beta-chloroethyl-2',4',5'-trichlorobenzenesulfonate which was previously disclosed in the prior art is included in Table IV for comparative purposes.

Table IV

| Compound | TGA Results Temperature at which weight change occurs, °C. | | | | |
|---|---|---|---|---|---|
| | 5% wt. Loss | 10% wt Loss | 25% wt Loss | 50% wt Loss | 75% wt Loss |
| tris-(2,2,2-bromomethyl) ethyl-2',4',5' trichlorobenzene sulfonate | 258° C. | 276° C. | 300° C. | 320° C. | 335° C. |
| 1,3-bis-(2',4',5',-trichloro-benzene sulfonato)-2,2-bis-(bromoethyl)propane | 305° C. | 320° C. | 345° C. | 367° C. | 387° C. |
| beta-chloroethyl-2',4',5'-trichlorobenzene sulfonate | 193 | 218 | 247 | 267 | 284 |

Based on this disclosure many other modifications and ramifications will naturally suggest themselves to those skilled in the art. There are intended to be comprehended as within the scope of this invention.

The embodiments of the invention in which an exclusive property or privilege is claimed are defined as follows:

1. A halobenzene sulfonate of the formula

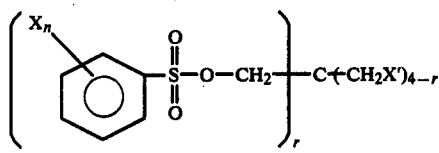

wherein X and X' are independently selected halogen, n is an integer of from 1 to 5, and r is an integer of from 1 to 4.

2. The halobenzene sulfonate of claim 1 wherein the halogen is chlorine and bromine.

3. The halobenzene sulfonate of claim 1, wherein said halobenzene sulfonate is tris-(2,2,2-bromomethyl)ethyl-2',4',5'-trichlorobenzene sulfonate.

4. The halobenzene sulfonate of claim 1 wherein said halobenzene sulfonate is 1,3-bis-(2',4',5'-trichlorobenzene sulfonato)-2,2-bis-(bromomethyl) propane.

5. The halobenzene sulfonate of claim 1 wherein said halobenzene sulfonate is 1,3-bis-(2',5'-dibromobenzene sulfonato)-2,2-bis-(bromomethyl) propane.

6. The halobenzene sulfonate of claim 1 wherein said halobenzene sulfonate is tris(2,2,2-bromomethyl) ethyl-2',5'-dibromobenzene sulfonate.

7. A flame retardant plastic polymer composition comprising a polymer and a flame retarding amount of a sulfonate compound of claim 1.

8. The composition of claim 7 wherein the halogen is chlorine and bromine.

9. The composition of claim 7 wherein said polymer is selected from the group comprising polyurethane, polystyrene and polyolefin polymers.

10. The composition of claim 9 wherein said compound is tris-(2,2,2-bromomethyl) ethyl-2',4',5'-trichlorobenzene sulfonate.

11. The composition of claim 9 wherein said compound is 1,3-bis-(2',4',5'-trichlorobenzene sulfonato)-2,2-bis-(bromomethyl)propane.

12. The composition of claim 9 wherein said compound is 1,3-bis-(2',5'-dibromobenzene sulfonato)-2,2-bis-(bromomethyl) propane.

13. The composition of claim 9 wherein said compound is tris-(2,2,2-bromomethyl) ethyl-2',5'-dibromobenzene sulfonate.

* * * * *